United States Patent [19]

Melcher et al.

[11] Patent Number: 4,814,690
[45] Date of Patent: Mar. 21, 1989

[54] APPARATUS AND METHODS FOR MEASURING PERMITTIVITY IN MATERIALS

[75] Inventors: James R. Melcher, Lexington, Mass.; Mark C. Zaretsky, Brooklyn, N.Y.

[73] Assignee: Massachusetts Institute of Technology, Cambridge, Mass.

[21] Appl. No.: 104,179

[22] Filed: Oct. 2, 1987

[51] Int. Cl.⁴ .................. G01R 27/26; G08C 19/10; G08C 19/16
[52] U.S. Cl. ................ 324/61 R; 340/870.37
[58] Field of Search ............... 324/61 R, 61 P, 61 QS; 340/870.37; 364/500; 422/62, 108, 119; 204/192.13

[56] References Cited

U.S. PATENT DOCUMENTS

| | | | |
|---|---|---|---|
| 4,058,766 | 11/1977 | Vogel et al. | 324/61 R |
| 4,399,100 | 8/1983 | Zsolnay et al. | 422/62 |
| 4,423,371 | 12/1983 | Senturia et al. | 324/61 R |
| 4,496,697 | 1/1985 | Zsolnay et al. | 526/60 |

OTHER PUBLICATIONS

Zaretsky et al., *Lees Technical Report*, pp. 1-43, Jul. 1986.

*Primary Examiner*—Reinhard J. Eisenzopf
*Assistant Examiner*—Walter E. Snow
*Attorney, Agent, or Firm*—Thomas J. Engellenner

[57] ABSTRACT

Devices and analytical techniques are disclosed for measuring the spatial profile of permittivity of a material by multiple wavenumber interrogations. Electrode structures are disclosed which define a number of different fundamental wavelengths (or wavenumbers). Spatially periodic interrogation signals (of temporary frequency "$\omega$") from the electrode structures are attenuated to varying degrees by the material undergoing analysis, depending upon the wavenumber ("$k$"), thereby permitting the derivation of a composite dielectric profile.

19 Claims, 4 Drawing Sheets

APPARATUS AND METHODS FOR MEASURING PERMITTIVITY IN MATERIALS

BACKGROUND OF THE INVENTION

The technical field of this invention is dielectrometry and, in particular, the spatial interrogation of materials to deduce their physical properties from complex permittivity measurements.

Dielectric measurement of materials during manufacturing and the like is becoming increasingly commonplace. For example, on-line monitoring devices are now available for measuring the progress of curing in parts molded from polymeric composites. Such monitors typically are embedded into a portion of the part which will be trimmed off during subsequent finishing operations. By measuring changes in the complex dielectric permittivity of the composite, the state of curing can be deduced. Such sensors can be used to control or modify various manufacturing parameters, such as the heating and/or cooling rates, or the amount of applied pressure.

It is known in the art that A.C. measurements of dielectric properties by sensors implanted within a curing polymer can provide useful data on curing and other material properties. In particular, U S. Pat. No. 4,423,371 issued to Senturia et al. in December, 1983, discloses that A.C. measurements in the frequency range of 1 Hz to 10 kHz can be reliable indicators of curing. See also U.S. Pat. No. 4,399,100 issued to Zsolnay et al. in August, 1983, and U.S. Pat. No. 4,496,697 issued to Zsolnay et al. in January, 1985, for further disclosures of automatic process control systems for curing polymeric materials.

Conventional sensors for measuring changes in the dielectric properties of a curing polymer are typically either formed as simple parallel plate capacitors, such as those disclosed in U.S. Pat. Nos. 4,399,100 or 4,496,697 or planar interdigitated capacitors, such as those disclosed in U.S. Pat. No. 4,423,371. The utility of these sensors is limited by their inability to provide enough information to resolve distributions of parameters. The deduction of inhomogeneities is sometimes attempted from temporal frequency response information, but this process does not give a unique distribution and cannot be implemented without assuming that the frequency dispersion of the material in question is known.

There exists a need for better permittivity measuring devices and methods. In particular, there exists a need for better devices and methods for conducting non-destructive interrogations of materials to determine their physical properties across a spatial profile.

SUMMARY OF THE INVENTION

Devices and analytical techniques are disclosed for measuring the spatial profile of permittivity of a material by multiple wavenumber interrogations. Electrode structures are disclosed which define a number of different fundamental wavelengths (or wavenumbers). Spatially periodic interrogation signals (of temporary frequency "$\omega$") from the electrode structures are attenuated to varying degrees by the material undergoing analysis, depending upon the wavenumber ("k"), thereby permitting the derivation of a composite dielectric profile.

The techniques described herein are referred to as an "imposed $\omega$-k" approach to dielectrometry. A spatially periodic field is imposed upon the material via an electrode structure under the control of a wavenumber controller. The electrode structure can be at the material surface or embedded. The electrodes are also used to measure the effect of the material on a charge induced on the electrodes in response to this field. By varying the wavenumber k, a spatial distribution of complex permittivity is deduced as a function of the temporal frequency $\omega$, when the property depends only on the coordinate distance, x, perpendicular to the electrode structure.

Sensors, according to present invention, are useful not only in the monitoring of polymer curing and the manufacture of parts which do not permit sensors to be embedded, but also in the monitoring of various other material changes, such as the outgassing of solvents from paints, the removal of moisture from coatings, the diffusion of dopants into semiconductors, and deposition of materials, generally.

In one illustrated embodiment, the electrode structure can be formed by an array of concentrically-wound, spiraling electrodes, and the wavenumber controller can be implemented by electronic switches which apply voltages to subsets of the electrodes to define fundamental wavenumbers. In another illustrated embodiment, the electrode array comprises a plurality of different-sized, discrete electrode pairs (e.g., interdigitated pairs) which define a plurality of fundamental wavenumbers. In either case, a permittivity analyzer compares the resulting response sensed by the electrode array at different wavenumbers to predictions based on a postulated model in order to derive a spatial profile of permittivity in the material.

The invention will next be described in connection with certain illustrated embodiments; however, it should be appreciated that various modifications, additions and subtractions can be made by those skilled in the art without departing from the spirit or scope of the invention. For example, in one illustrated embodiment, a "square spiral" of concentrically-wound electrodes is shown. It should be clear that the electrode array can take various other spiraling (i.e., "round spiral") alternative geometric shapes so long as subsets of the electrodes are capable of defining different wavenumbers for purposes of interrogation of the material.

Moreover, analogous apparatus and methods can be employed based on measurements of inductance and the magnetic permeablility of the materials, films, coatings, etc. to electrically-induced magnetic fields at varying wavelengths. In a magnetic system, magnetic fields induce a complex inductance response in the material undergoing study which can be used to deduce the spatial profile by analogous inductance analysis.

The techniques disclosed herein can also be used to deduce the mechanical properties of materials or the properties of inhomogeneous electromechanical continua, such as diffuse double layers or biphasic media. Furthermore, the techniques for estimating the spatial profile can be based on parametric models of various types, such as linear and exponential distributions of permittivity, step functions, and piecewise continuous exponentials and piecewise linear functions. In addition, the techniques disclosed herein for deducing one dimensional spatial profiles can be extended to two and three dimensional interrogations.

DETAILED DESCRIPTION

Figure 1:
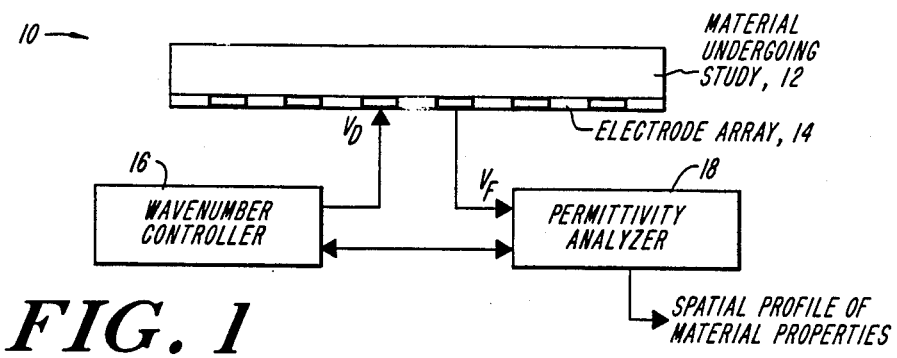
FIG. 1 is an overall schematic diagram of a dielectric analyzing apparatus according to the present invention.

In conventional dielectrometry, the temporal frequency response is used to study electrical attributes of materials, such as can be discerned through the effect on the fields of molecular and domain-level polarization and of ionic conduction (for examples). In conventional dielectric sensors, Plane Parallel electrodes and a voltage source, v, are used to impose an electric field, $\overline{E}$, on a sample. With the charge on the driven electrode of this conventional apparatus defined as q, so that the current, i=dq/dt, the response to a sinusoidal drive having the frequency $\omega$ can be defined as $$\hat{C}(\omega) = \hat{q}/\hat{v} \quad (1)$$

where $\hat{v}$ and $\hat{q}$ are the complex amplitudes of the charge and voltage.

In complex notation, the electroquasistatic fields in the material are described by Gauss' Law $$\nabla \cdot \hat{\epsilon}\hat{E} = 0 \quad (2)$$

where $\hat{\epsilon} = \hat{\epsilon}(x)$ and the requirement that $\hat{E}$ be irrotational and, hence, related to the complex amplitude of the Potential, $\hat{\Phi}$, by $$\hat{E} = -\Delta\hat{\Phi} \quad (3)$$

Guard electrodes, having the same potential as the driven electrode, are often used to make E have only an x component. This is done in an attempt to make the electric field imposed on the sample to be uniform. However, the complex permittivity, $\hat{\gamma}$, often actually varies with x. As a result, the electric field varies with x, and the sample cannot be subjected to a uniform field. The effect of the non-uniform permittivity is evident in the measured temporal frequency response which can be derived by writing Eqs. (2) and (3), respectively $$\frac{d(\hat{\epsilon}\hat{E}_x)}{dx} = 0 \quad (4)$$

$$\hat{E}_x = -\frac{d\hat{\Phi}}{dx} \quad (5)$$

Integration of these from a first planar electrode where x=o, to the second Parallel plate electrode at x=h, and use of the conditions that the potential be zero at x=o and be the applied voltage, $\hat{V}$, at x=h, gives the capacitance:

$$\hat{C}(\omega) = \frac{\hat{q}}{\hat{v}} = A\left[\int_0^h \frac{dx}{\epsilon(x)}\right]^{-1} \quad (6)$$

where the area of the first electrode is A. Measurement of $\hat{C}(\omega)$ at a single temporal frequency therefore gives at best a spatial average of the complex permittivity. With assumptions concerning the frequency dependence of the local complex permittivity, it is possible to use the full temporal frequency response to distinguish between certain attributes of the non-uniformity. However, the necessity for making assumptions of this type strongly limits what additional information can be obtained concerning the physical mechanisms underlying the complex permittivity (such as molecular or ionic dynamics). Moreover, even with these assumptions, there is no unique relationship between the actual spatial distribution of complex permittivity and the temporal frequency response. This follows from Eq. 6 which makes it evident that at a given frequency there are many different distributions giving rise to the same complex capacitance. Contributions to the integral coming from the neighborhood at x=a can be interchanged with those at x=b (where a and b are any pair of values between x=o and x=h), and the integral will be the same. Hence, there can be no unique inference of the spatial distribution from the temporal frequency response alone.

In the present invention, devices and methods are disclosed for using the spatial frequency response (the response as a function of the dominant wavenumber k) to deduce the spatial distribution of complex permittivity (as a function of temporal frequency k) when that property depends only on the coordinate, x, perpendicular to the electrode structure. This approach exploits a property of electroquasistatic fields. If the fields are made to be periodic in one direction, y (the direction of periodicity in the plane of an electrode array), they generally decay in the perpendicular direction, x, at a rate that is inversely proportional to the wavelength, $\lambda = 2\pi/k$. Thus, if a spatially periodic array of electrodes is used to impose a potential and sense the resulting charge induced on its surface, the response to the short wavelengths will reflect the permittivity of the material in the immediate vicinity of the electrodes. The longer-wave electrodes will not only sample the permittivity of the immediately adjacent material but that further out as well. As the wavelength is further increased, the permittivity at an increasing range from the sensing surface will influence the measurement. Disclosed in the following is apparatus and method for efficiently reconstructing the permittivity profile from measurements made as a function of wavenumber (wavelength).

In one "imposed $\omega$-k" dielectrometry apparatus 10 shown in FIG. 1, a spatially periodic field is imposed on a material 12 by means of an array of electrodes 14 at the surface of the material. The electrode array can be formed on a substrate of insulating material backed by a highly conducting material. The sample 12, which in general is non-uniform in the direction, x, perpendicular to the array is shown just above the electrodes. In the apparatus shown, a subset of electrodes is driven with the sinusoidally varying voltage $V_D$ by wavenumber controller 16 while another subset is connected to high-impedance electronics of permittivity analyzer 18 that measure the potential $V_F$. Alternately, these latter electrodes can be terminated in an arbitrary load and a measurement provided by analyzer 18 of either a sensed voltage or current.

Figure 2:
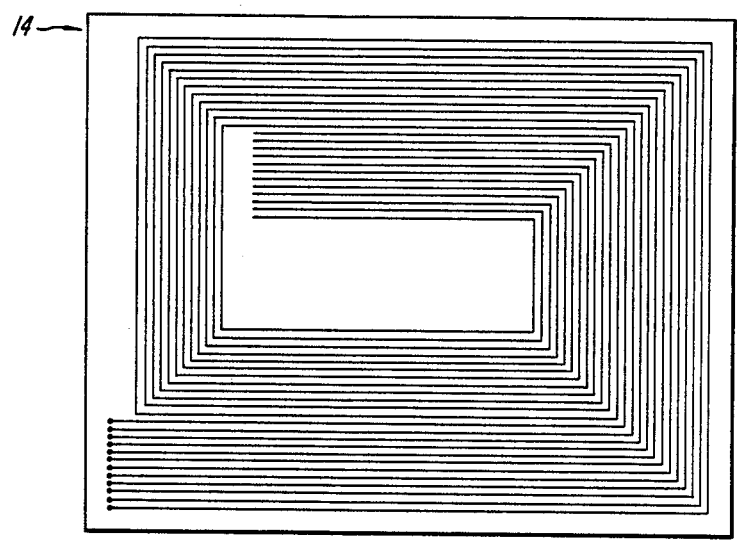
FIG. 2 is a schematic top view of an electrode array for use in the apparatus of FIG. 1.
Figure 3:
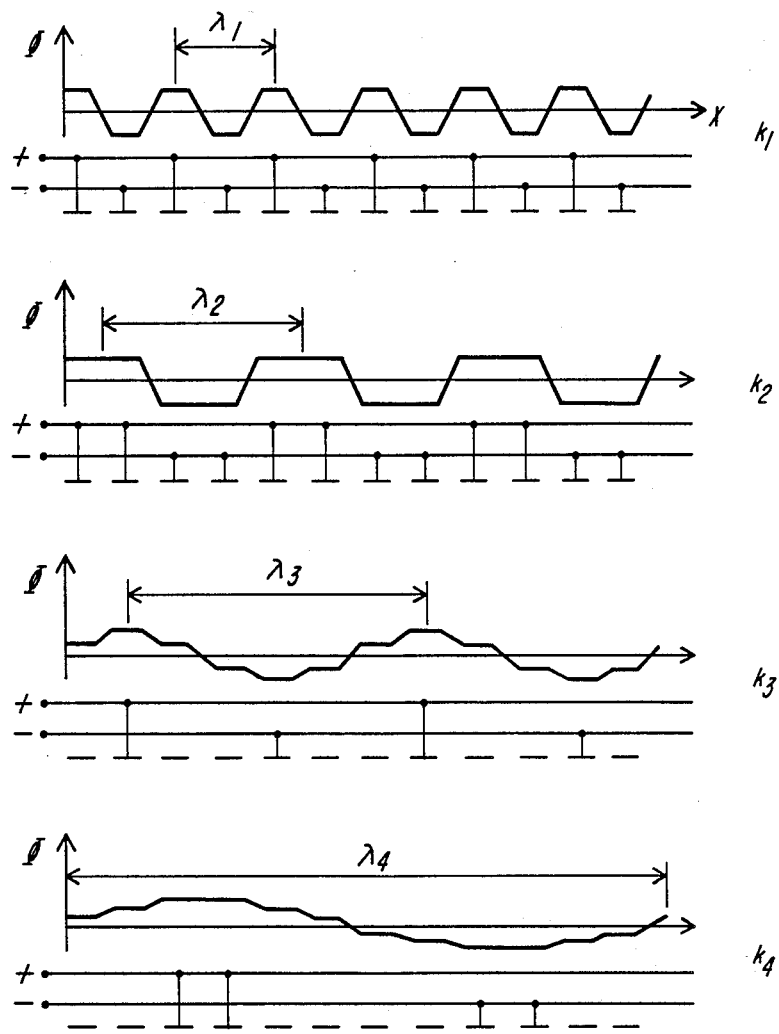
FIG. 3 is a schematic illustration of wavenumber control circuitry and resulting waveforms for use in the apparatus of FIG. 1.

An electrode system which can be conveniently constructed on a single surface and in which the wavelength is varied by terminal connections is shown in FIG. 2. In the example shown, twelve electrodes form a spiral with the direction, y, of periodicity the radial directions, respectively perpendicular to the four segments comprising one spiral. Connected for the shortest wavelength, the electrodes have the potential shown by switch position $k_1$, at the top in FIG. 3. In this twelve electrode system, there are four wavelengths that can be obtained by appropriate connection of the electrode terminations, as illustrated in FIG. 3 by $k=k_1 \ldots k_4$.

Figure 4:
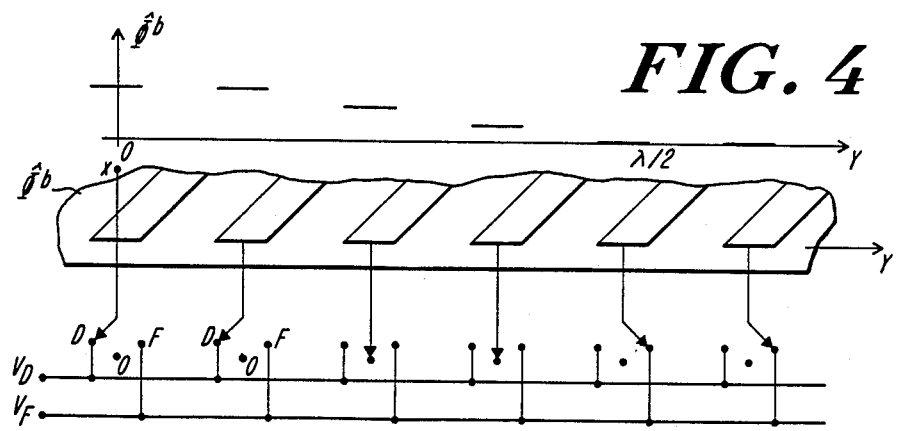
FIG. 4 is a schematic illustration of alternative wavenumber control circuitry and resulting waveforms for use in the apparatus of FIG. 1.

An alternative wavenumber control system that achieves a variable wavelength by switching the individual electrode terminations is shown in FIG. 4. In the sketch of the electrode-plane potential distribution located above the structure in FIG. 4, the connections have been made so that ten electrodes comprise a wavelength with three having the potential of $V_D$, three at $V_F$ potential and four floating. These latter electrodes are used to prevent the higher harmonics (incurred because of the coupling between the edges of adjacent electrodes) from dominating the response. In other schemes for minimizing the effects of higher harmonics, guard electrodes can be employed at the same potential as the sensor electrodes.

Figure 5:
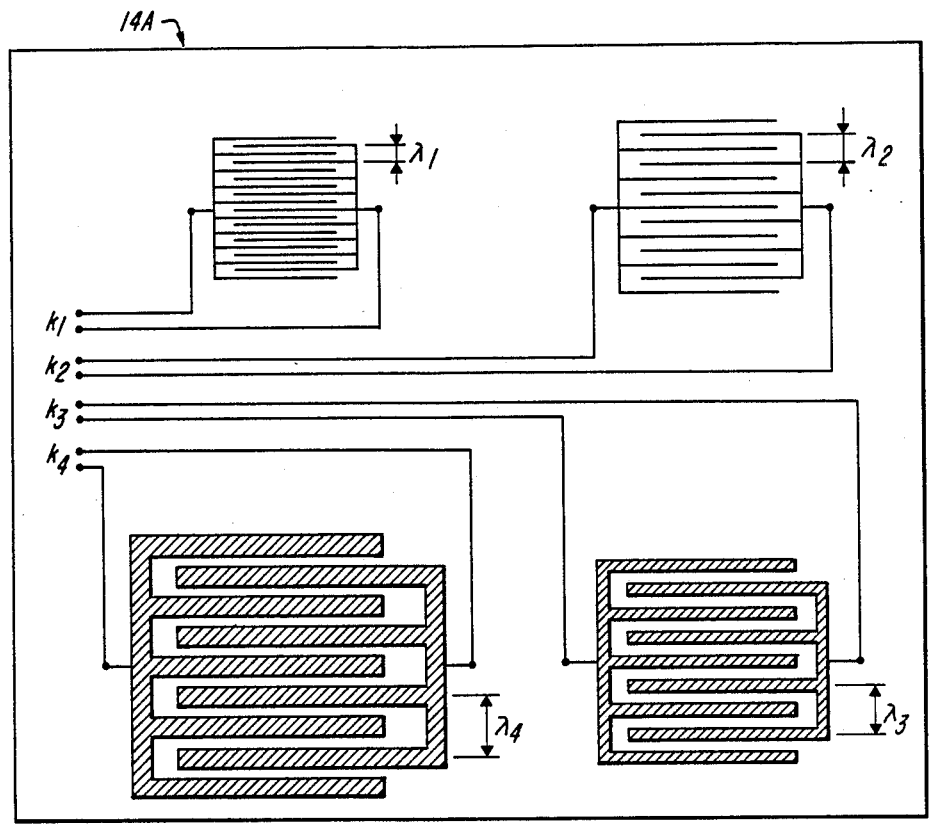
FIG. 5 is a schematic top view of an alternative electrode array for use in the apparatus of FIG. 1.

An alternative embodiment is shown in FIG. 5 where the electrode array consists of a set of different-sized discrete pairs of electrodes. In the illustrated embodiment of FIG. 5, the electrode pairs are interdigitated and again formed on a substrate of insulating material backed by a highly conductive material. Provided the sample facing the electrodes has the same permittivity profile adjacent to each pair, measurements taken from each provide the desired data. Measurements of the response of the electrode array define the gain G, which in general is a complex quantity reflecting both the magnitude and Phase of the response. In the case shown in FIG. 1, the gain might be defined as $V_F/V_D$. The data to be used in determining the distribution of complex permittivity consists of a set of gains, $G=G_m$, measured at the dominant wavenumber $k_j$, $j=1 \ldots N$.

$$G_{measured}=G_m(\omega,k_j), k=k_1 \ldots k_N \tag{7}$$

The dominant wavenumbers are related to the wavelength or periodicity length, $\lambda_j$, by $$k_j=2\pi/\lambda_j \tag{8}$$

The wavelength is illustrated by FIGS. 3 and 4. In the following, the data designated by the subscript, j, is taken as being in the order of increasing wavelength and, hence, decreasing wavenumber.

Various representations of the complex permittivity distribution can be used. For example, the distribution can be represented by layers, each having a uniform permittivity. Alternatively, each layer can have an exponential distribution. Included in each representation is the possibility of having complex surface permittivities at one or more of the interfaces. Without the complex surface Permittivities, the representations approximate the distribution by "stair-step" and piece-wise continuous functions, respectively.

The "direct problem" is the basis for inferring the distribution from the data. Here, the object is to predict the gain, given the distribution of permittivity. To prevent errors in deducing the distribution that are associated with the geometry of the electrode array, it is desirable to have a method of solving the direct problem that takes the finite width and spacing of the electrodes, as well as the properties of their substrate, into account. This is especially true if, as to be described next, the inversion procedure "marches" from short to long-wave lengths. Although finite difference and finite element numerical methods can be used to take into account the effects of geometry, a collocation technique based on a spatial Fourier decomposition of the fields has been shown to be well suited to the direct problem.

Using the Fourier decomposition approach, the mixed boundary value problem posed where the electrode array interfaces the media is solved by representing the potential distribution on that part of the interface between array and media that is between electrodes by a piece-wise continuous potential having collocation potentials, $V_j$, where the potentials are pieced together.

Given the distribution of material properties, the specific surface capacitance density, $C_n$ can be predicted. This is the complex electric displacement response of the media (at the plane of its interface with the electrode structure) to a complex potential in that plane having a purely sinusoidal spatial distribution with wavenumber $k_n$ and purely sinusoidal time variation, with angular frequency $\omega$. The fields above the electrodes and at the interface between the electrodes (where the possibility of having a surface complex permittivity, perhaps due to absorbed slightly ionized material at he interface between the electrodes) are also represented by their spatial Fourier components. These fields are then made self-consistent with those in the media by a numerical evaluation of the collection potentials, $V_j$, and this makes it possible to evaluate the admittance in the circuit. These admittances represent the response with arbitrary types of termination.

For the particular case where the gain is defined as the complex ratio of the output voltage to driving voltage, where $Y_{11}$, $Y_{12}$ and $Y_{22}$ are the admittance of the "pi" network now representing the combination of electrode array and media subject to measurement and $Y_l$ is the impedance of the circuit used to measure the output voltage, $$G = \frac{V_f}{V_D} = \frac{Y_{12}}{Y_{12} + Y_{11} + Y_l} \tag{9}$$

The same circuit elements can be used to predict the response current, as would be appropriate if the media were relatively lossy over the frequency range of interest.

Inversion methods build on having the capability for solving a family of direct problems. Inversion methods must deduce the discrete properties needed to complete the representation from the available discrete gain measurements made over an appropriate range of imposed dominant wavelengths. These are the gain measurement summarized by Eq. 7. In general, N gains are measured ranging over wavelengths short enough to resolve the distribution close to the array and ending at a wavelength long enough to make the field extend far enough into the material to reflect material properties to the desired depth. With properly designed electrodes and material properties that do not suffer extreme variations, profiles are sensed to a depth that is approximately a quarter wavelength. In general, the inversion method then provides for an identification of N parameters describing the permittivity distribution from these N measurements. In the case of a stair-step approximation, the distribution of complex permittivity would be represented by the N complex permittivities of the steps. In the case where (perhaps exponential) functions are pieced together in a continuous manner, the N identified permittivities could be those at the locations where the smooth distribution is pieced together. In any case, the introduction of complex surface permittivities imposes a requirement for additional data. Thus, with N measurements over an appropriate range of wavelengths, it would be possible to deduce N-S bulk parameters describing either the stair-step or the piece-wise distributions and S complex surface permittivities.

It is important to note that the inversion process can be carried out using measurements taken at the same frequency. Thus, the permittivity distributions can be deduced at each frequency. The information inherent to the temporal frequency response is therefore preserved and can be exploited for further parameter identification purposes. (An example would be to distinguish between polarization mechanisms and between polarization and ion migration phenomena as they occur at various depths in the media.)

The estimation of parameters from experimental data can be formalized by defining an error that is the difference between the measured gains and those predicted by the direct method:

$$e = G_{measured} - G(\theta)_{predicted} \tag{10}$$

Here, $\theta$ is a list of one or more parameters to be estimated and e is a column vector of errors associated with the different gains.

If, as in the illustration used here, there are as many measured gains as parameters to be determined, the estimation process then amounts to finding those values of $\theta$ that make $$e(\theta) = 0 \tag{11}$$

If there are more measurements than parameters so that the identification problem is overspecified, the estimation process can be represented as a minimization of a quadratic norm based on these errors and possibly a weighting function.

Figure 6:
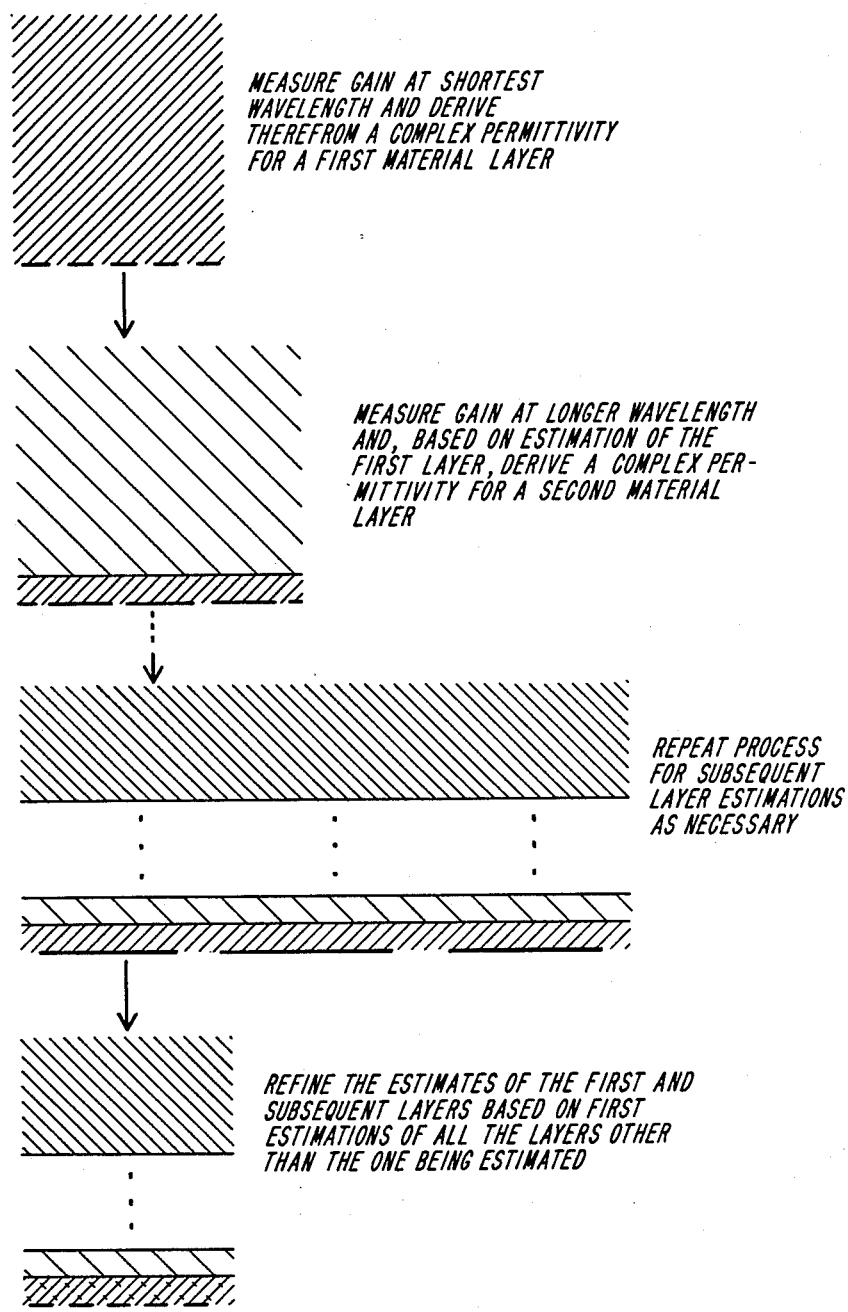
FIG. 6 is a flow diagram of a permittivity analyzer according to the present invention.

As shown in FIG. 6, the estimation problem can be reduced to a sequence of single parameter estimations (or perhaps two parameter estimations) by again exploiting the properties of quasistatic fields. For example, suppose the inhomogeneity is smooth. Then, the gain $G_m(k_1)$ measured at the shortest wavelength is used in conjunction with a single layer model to deduce the complex permittivity of the material nearest to the electrodes. With this parameter in hand, the complex permittivity of the material somewhat further out is determined from the gain $G_m(k_2)$ measured at the next longer wavelength. Like the first step, this one amounts to a single parameter estimation of the complex Permittivity of the second layer in a two-layer model for the media. Following this procedure, the measured gain $G_m(k_j)$ is used in conjunction with a model representing the complex permittivity by j parameters, the last of which is associated with the layer furthest from the electrodes (and about a quarter wavelength from the electrodes, based on the wavenumber of that measurement) to make a single parameter estimation. Once the first pass has been made through the data, working from short to long wavelengths and, hence, performing a sequence of single parameter estimations of the profile working outward from the electrodes, the parameters can be refined by passing through the data, again from short to long wavelengths. In these subsequent iterations, the parameters of layers other than the one being estimated are taken as being their values on the last estimation.

An optimal parameter estimation scheme takes advantage of all a priori knowledge of the complex permittivity distribution. For example, if it is known that the material actually consists of one or more discrete layers across the boundaries of which it is expected that the complex permittivity suffers an abrupt change, than a model can be used in which one or more of the layers represent the boundaries between actual Physical layers. If the location of such abrupt changes are not known, the parameter estimation scheme can then be one in which the location of such a boundary is one of the parameters being estimated. In some instances, the inversion can best be reduced to one or perhaps a sequence of multiple parameter estimations. For one skilled in the art, the single parameter estimation techniques desribed herein are readily generalized to the simultaneous estimation of multiple parameters.

We claim:

1. An apparatus for measuring the dielectric Properties of a material, the apparatus comprising:
   an array of electrodes capable of imposing an electric potential in a material and sensing a resulting electrical response;
   a wavenumber controller connected to said electrode array for applying voltage to subsets of said electrodes and thereby defining fundamental wavenumbers associated with said imposed electric potential in the material; and
   a permittivity analyzer connected to said wavenumber controller, including means for comparing the resulting responses sensed by said electrode array at different wavenumbers to predictions in order to derive a spatial profile of permittivity in the material.

2. The apparatus of claim 1 where in the array of electrodes comprises a plurality of concentrically-wound, spiraling electrodes.

3. The apparatus of claim 1 wherein the array of electrodes comprises a plurality of discrete electrode pairs defining a plurality of fundamental wavenumbers.

4. The apparatus of 3 wherein the electrode pairs are interdigitated electrode pairs.

5. The apparatus of claim 1 wherein the wavenumber controller further comprises a Plurality of electronic switches for applying at least one voltage to a subset of said electrodes of said array.

6. The apparatus of claim 5 wherein the switches further include means for applying two distinct voltages to separate subsets of the electrodes to define a fundamental wavenumber.

7. The apparatus of claim 6 wherein the switches further include means for defining floating electrodes.

8. The apparatus of claim 1 where the permittivity analyzer is a microcomputer programmed to measure the permittivity of the material at multiple wavelengths based upon a parametric model of the material and further includes means for performing iterative analyses to obtain a refined spatial profile.

9. A method for measuring the dielectric properties of a material, the method comprising:
   disposing an array of electrodes in contact with a material, the electrodes being adapted to impose an electric potential in the material and sense a resulting electric response;

interrogating the material at multiple wavelengths defined by subsets of said electrodes; and sensing the resulting electrical response at multiple wavelengths to derive a spatial profile of at least one property of the material.

10. The method of claim 9 wherein the step of interrogating the material further includes sequentially interrogating the material at multiple wavelengths.

11. The method of claim 9 wherein the step of interrogating the material further includes simultaneously interrogating the material at multiple wavelengths.

12. The method of claim 9 wherein the step of sensing the electrical response to derive a spatial profile further includes measuring the gain at the shortest wavelength to derive a profile estimation for a first material layer; and measuring the gain with at least one longer wavelength to derive a profile estimation for a subsequent material layer.

13. The method of claim 12 wherein the method further includes employing a parametric model to obtain said estimations for the first and subsequent material layers.

14. The method of claim 13 wherein a linear model is employed to represent the layers.

15. The method of claim 13 wherein an exponential model is employed to represent the layers.

16. The method of claim 13 wherein a continuous model is employed to represent the layers.

17. The method of claim 13 wherein a step function model is employed to represent the layers.

18. The method of claim 13 wherein the method further includes refining the estimate of each layer based on a prior estimation of all the layers other than the one being refined.

19. The method of claim 18 wherein the step of refining the estimate is iteratively repeated for each layer until a best fit to a parametric model is obtained.

* * * * *

UNITED STATES PATENT AND TRADEMARK OFFICE
CERTIFICATE OF CORRECTION

PATENT NO. : 4,814,690
DATED : March 21, 1989
INVENTOR(S) : James R. Melcher and Mark C. Zaretsky It is certified that error appears in the above-identified patent and that said Letters Patent is hereby corrected as shown below:

Column 3, line 42, "E" should read --$\hat{\bar{E}}$--.

Column 3, line 65, in Equation (6), "$\varepsilon$" should read --$\hat{\varepsilon}$--.

Column 4, line 29, "temporal frequency k" should read --temporal frequency $\omega$--.

Column 6, line 28, "he" should read --the--.

Column 8, lines 24-25, "Properties" should read --properties--.

Signed and Sealed this

Second Day of January, 1990

Attest:

JEFFREY M. SAMUELS

*Attesting Officer*   *Acting Commissioner of Patents and Trademarks*